United States Patent [19]

Xalabarder Miramanda

[11] Patent Number: 4,900,515
[45] Date of Patent: Feb. 13, 1990

[54] ARRANGEMENT FOR DETERMINING BLOOD CELL SEDIMENTATION RATE

[76] Inventor: Fernando Xalabarder Miramanda, Pau Casals 8-10,, 08140-Caldes de Montbui (Barcelona), Spain

[21] Appl. No.: 940,618

[22] Filed: Dec. 11, 1986

[30] Foreign Application Priority Data

Dec. 19, 1985 [ES] Spain ..................................... 291.154

[51] Int. Cl.$^4$ .............................................. B01L 3/02
[52] U.S. Cl. .................................. 422/100; 73/864.02; 73/864.03; 436/70; 436/181
[58] Field of Search .................. 436/70, 181; 422/100; 73/864.02, 864.03

[56] References Cited

U.S. PATENT DOCUMENTS

| | | | |
|---|---|---|---|
| 1,678,540 | 7/1928 | Trenner | 73/864.02 |
| 2,396,470 | 3/1946 | Mortensen | 422/100 |
| 2,809,773 | 10/1957 | Bender | 73/864.03 |
| 3,748,909 | 7/1973 | Kuo | 422/100 |
| 3,837,376 | 9/1974 | Brown et al. | 422/100 |
| 3,891,392 | 6/1975 | Betts et al. | 73/864.02 |
| 4,197,735 | 4/1980 | Munzer et al. | 422/100 |
| 4,248,830 | 2/1981 | Kallies et al. | 422/100 |
| 4,299,795 | 11/1981 | Bates | 422/100 |
| 4,332,768 | 6/1982 | Berglund | 422/100 |

FOREIGN PATENT DOCUMENTS 7601839  8/1977  Netherlands ...................... 436/70

Primary Examiner—Barry S. Richman
Assistant Examiner—Timothy M. McMahan
Attorney, Agent, or Firm—Staas & Halsey

[57] ABSTRACT

An arrangement for determining the blood cell sedimentation rate, comprising a pipette having at the upper end thereof a levelling device; a tube and a plunger sealingly engaging the outside wall of the pipette and having a diameter generally the same as the inside diameter (d) of the tube. The plunger is inserted in the tube at a distance from the lower end of the pipette such that when the plunger is inserted in the tube until such lower end of the pipette abuts the bottom end of the tube, it displaces blood into the pipette capable of filling the pipette without overflowing from the ensemble formed by the pipette plus the levelling device.

1 Claim, 1 Drawing Sheet

ARRANGEMENT FOR DETERMINING BLOOD CELL SEDIMENTATION RATE

BACKGROUND OF THE INVENTION

1. Field of the Invention

The present invention relates to an arrangement for determining the sedimentation rate of blood cells, comprising a standardised graduated pipette of volume $V_1$, having a lower free end and an upper end provided with a levelling device of volume $V_2$ adapted to receive and retain any excess blood introduced in the pipette; a plastics plunger sealingly adapted to the outer surface of the pipette and having an active edge; and a tube having a closed bottom end, a height h and an inside diameter d, the tube being adapted to contain the blood to be analysed, the inside diameter d of the tube being generally the same as the outside diameter of said active edge of the plunger, such that the plunger is adapted to slide within said tube while sealingly engaging the wall thereof.

SUMMARY OF THE INVENTION

The determination of the blood cell sedimentation rate is based on obtaining a relatively very accurate amount of blood. It is an object of the invention to allow this requirement to be fulfilled in a fast, convenient and reliable way.

To attain such object an arrangement of the type described above has been devised and is characterized in that the distance a between the active edge of the plunger and the free lower end of the pipette inserted in the tube is such as to fulfil generally the following relationship:

$$V_1 \leq \pi/4\, d^2\, (h-a) \leq V_1 + V_2$$

whereby the cylindrical space of height e, generally equivalent to $h-a$ and covered by the plunger inside the tube until the bottom end of the pipette abuts the closed bottom end of the tube, corresponds to a volume of blood expelled from the tube capable of filling the pipette without exceeding the filling of the whole formed by said pipette plus the levelling device.

BRIEF DESCRIPTION OF THE DRAWINGS

To facilitate the understanding of the foregoing, reference is made hereinafter to the accompanying drawings which, in view of their explanatory nature, are to be deemed to be lacking in any limitative nature relative to the scope of legal protection being applied for. In the drawings.

DETAILED DESCRIPTION OF THE INVENTION

Figure 1:
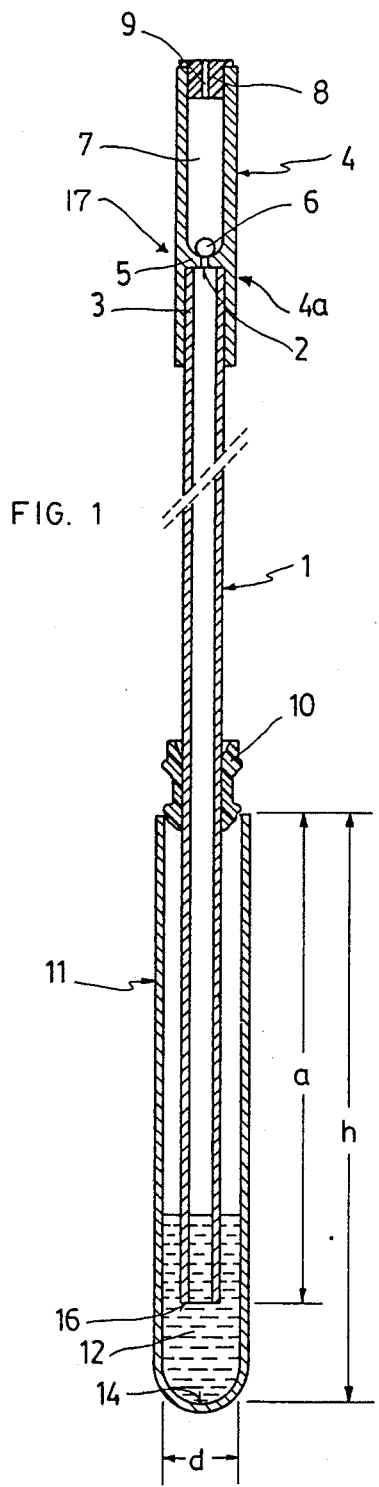
FIG. 1 is an axial sectional view of the whole arrangement, comprising pipette, plunger and tube in the position corresponding to the start of insertion of the plunger in the tube.

As is well known, the test or analysis for determining the blood cell sedimentation rate uses as the most important element thereof a standardised graduated pipette 1. Said pipette has a capacity $V_1$ of about 1 cubic centimeter and is graduated along a scale the start 2 of which is at the top end 3.

The pipette is filled with blood up to the start of the scale, is closed at the bottom end and is allowed to rest in a vertical position. The red blood cells settle out in the plasma and a reading of the sediment level is taken at appropriate time intervals, providing thereby the necessary data for the determination of the blood sedimentation rate.

Certain difficulties arise for filling the pipette 1 exactly up to the start 2 of the scale, whereby the top end or portion 3 is frequently provided with a levelling device 4 (which may adopt different forms) for receiving and retaining any excess blood forced into the pipette.

The levelling device 4 shown in the drawings is described without any limitative condition. It is provided with means 4a for attachment thereof to the pipette 1; a transverse wall 5 having a ball 6 forming a valve allows blood to be drawn into the chamber 7 of volume $V_2$. This chamber is closed at the top end thereof with a stopper 8 having a breather passage 9, such that the pipette 1 may be filled with blood, together with a small excess amount occupying the chamber 7, by suction, pressure or any other system. At the end of the filling operation, the blood in the chamber is retained by the valve 17 including elements 5,6, whereby it does not participate in the sedimentation taking place in the pipette itself.

From the foregoing, there is gathered the advantage represented by the use of the levelling device 4, since the need of an extreme accuracy on filling the pipette 1 is avoided.

Furthermore, it is also frequent not to use suction for filling the pipette; for this purpose, there is known the use of a resilient plunger 10 sealingly engaged around the outside of the pipette 1. When the plunger 10 is inserted in a tube 11, it acts as a piston to displace part of the blood 12 contained in the tube towards the pipette.

Notwithstanding, in the known prior art, one has to pay close attention when inserting the plunger, to make sure that it is not inserted too little (whereby the pipette would not be filled), nor too much, in which case the pipette and levelling device 4 would be filled, with blood overflowing through the breather passage 9.

Figure 2:
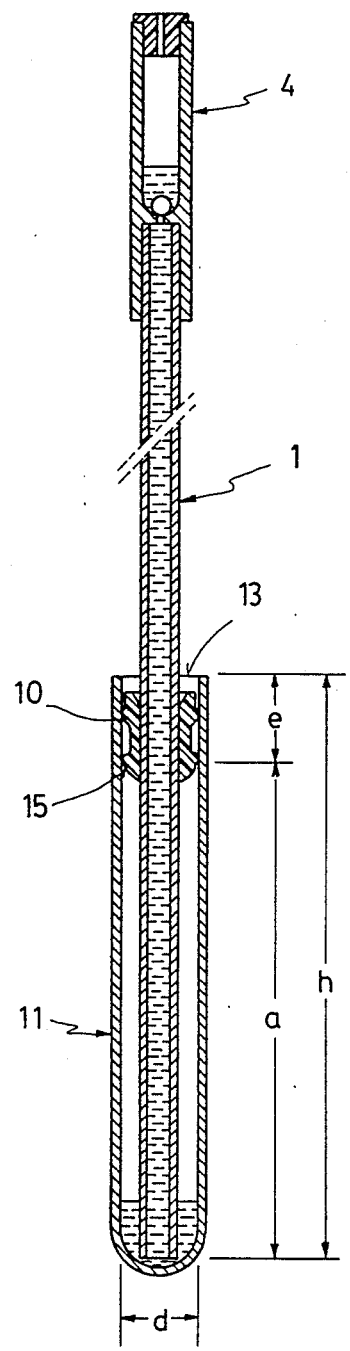
FIG. 2 is a cross sectional view similar to FIG. 1 but corresponding to the position of maximum insertion, in which the end of the pipette reaches the bottom of the tube.

To ensure a rapid, reliable performance of this operation is an object of the invention. The height of the tube 11 is h, comprised between the open end 13 and the bottom end 14; d is the inside diameter of the tube and is substantially the same as the outside diameter of the plunger 10; a is the distance between the active lower edge 15 of the plunger and the free lower end 16 of the pipette; and e is the distance covered by the plunger 10 in the pipette, from its insertion therein (FIG. 1) until the lower end 16 of the pipette abuts the bottom end 14 of the tube (FIG. 2).

It is to be appreciated that e (FIG. 2) is substantially the same as the difference between the height h and the distance a, since the space remaining between the end 16 (in the position of maximum insertion of the pipette) and the bottom end 14 is negligible, due to the curving of the tube.

According to the invention, the plunger 10 is placed in such a way that the distance a between the active lower edge 15 and the end 16 of the pipette is such as to meet the following expression:

$$V_1 \leq \pi/4d^2 (h-a) \leq V_1+V_2$$

Since e is the same as $h-a$, the distance covered by the plunger 10 within the tube 11 corresponds to a cylindrical volume equal to:

$$\pi/4d^2 e$$

whereby (ignoring insignificant questions of air compression), if such volume is the same as or greater than $V_1$ (i.e. the volume of the pipette), such displacement is sufficient to fill the pipette; furthermore, such volume is less than or equal to $V_1+V_2$, whereby such displacement is incapable of filling the pipette 1 plus the levelling device 4, thereby preventing an overflow of blood through the breather passage 9.

The above described arrangement provides a convenient, rapid, reliable system for preparing blood cell sedimentation rate determinations. The extracted blood sample is placed in a tube 11; a pipette 1 having a correctly positioned plunger 10 and of the necessary diameter is inserted in the tube; when the end 16 of the pipette abuts the bottom end 14 of the tube, the tube has been filled adequately. Then, the arrangement, i.e. the ensemble of tube and pipette, is placed in a vertical position and everything is adequately prepared for the blood cell sedimentation rate determination.

What I claim is:

1. An arrangement for determining the blood cell sedimentation rate, comprising:
   a standardized graduated pipette having a volume $V_1$, with a free lower end and an upper end;
   a levelling device of volume $V_2$ including one-way valve means for connecting the upper end of the pipette to the levelling device, for receiving and retaining blood from the pipette and for preventing the flow of blood from the levelling device to the pipette;
   a resilient plunger sealingly engaged with the outside of the pipette and having an active edge and an outside diameter; and
   a tube having a closed bottom end, a height h and an inside diameter d, the inside diameter d of the tube being generally the same as the outside diameter of said active edge of the plunger, such that the latter is slidable within said tube while being sealingly engaged therewith, the distance a between the active edge of the plunger and the free lower end of the pipette inserted in the tube satisfies the following relationship:

$$V_1 \leq \pi/4d^2 (h-a) \leq V_1+V_2$$

and wherein a cylindrical space of height e, generally equivalent to $h-a$ and covered inside the tube until the free lower end of the pipette abuts the closed bottom end of the tube, corresponds to a volume of blood expelled from the tube, through said valve means and into said levelling device, capable of filling the pipette without overfilling the unit formed by said pipette and the levelling device.

* * * * *